United States Patent [19]

Rossetto

[11] Patent Number: 5,104,372
[45] Date of Patent: Apr. 14, 1992

[54] DEVICE FOR CLOSING THE CONTAINMENT WELL OF A BLOOD CENTRIFUGATION CELL IN A CENTRIFUGAL MACHINE

[75] Inventor: Giorgio Rossetto, Melara, Italy

[73] Assignee: Dideco S.p.A., Modena, Italy

[21] Appl. No.: 549,474

[22] Filed: Jul. 6, 1990

[30] Foreign Application Priority Data

Jul. 31, 1989 [IT] Italy ................................ 21386 A/89

[51] Int. Cl.$^5$ .......................... B04B 3/08; B04B 7/02
[52] U.S. Cl. ...................................... 494/38; 494/60; 366/347
[58] Field of Search ................... 366/347; 494/39, 61, 494/85, 38, 43, 60; 220/333, 332, 329; 220/263, 264, 291, 331, 335, 336, 252, 253, 245, 246, 254, 255, 256

[56] References Cited

U.S. PATENT DOCUMENTS

| | | | |
|---|---|---|---|
| 1,152,286 | 8/1915 | Brownson | 220/336 |
| 2,261,936 | 11/1941 | Johnson | 494/60 |
| 2,670,898 | 3/1954 | Pickels | 494/61 |
| 3,480,311 | 11/1969 | Lanham | 220/246 |
| 3,481,506 | 12/1969 | Vevirit | 220/264 |
| 3,848,769 | 11/1974 | Beil | 220/333 |
| 3,963,438 | 6/1976 | Banez | 220/336 |
| 4,377,245 | 3/1983 | Patty | 220/336 |
| 4,561,563 | 12/1985 | Woods | 220/336 |
| 4,815,066 | 3/1989 | Horvath | 220/264 |

Primary Examiner—Harvey C. Hornsby
Assistant Examiner—James F. Hook
Attorney, Agent, or Firm—P. C. Richardson; L. C. Akers; R. C. Turner

[57] ABSTRACT

The invention discloses a device for closing the inlet of a containment well of a blood centrifugation cell in the body of a centrifugation machine. A plate is supported at one end of the inlet of the containment well and is rotatable about the horizontal axis. The plate has a pair of parallel pins extending perpendicularly from the surface. A pair of half-lids are each pivotably supported at one end thereof by one of the pins, and have matable inner edges. The closing device includes apparatus for locking the half-lids into a closure position, whereby the half-lids are rotated downwardly against the inlet with the half-lids pivoted together, thereby closing the inlet of the containment well.

5 Claims, 2 Drawing Sheets

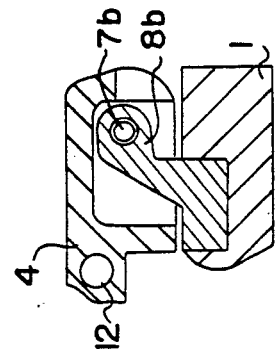
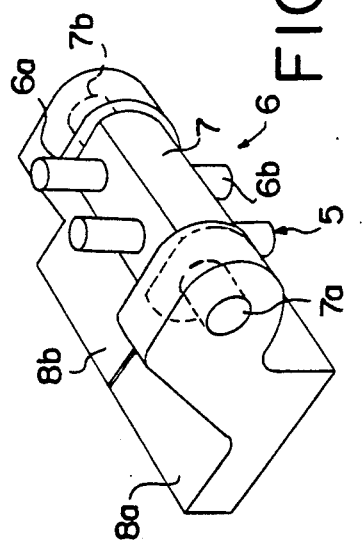
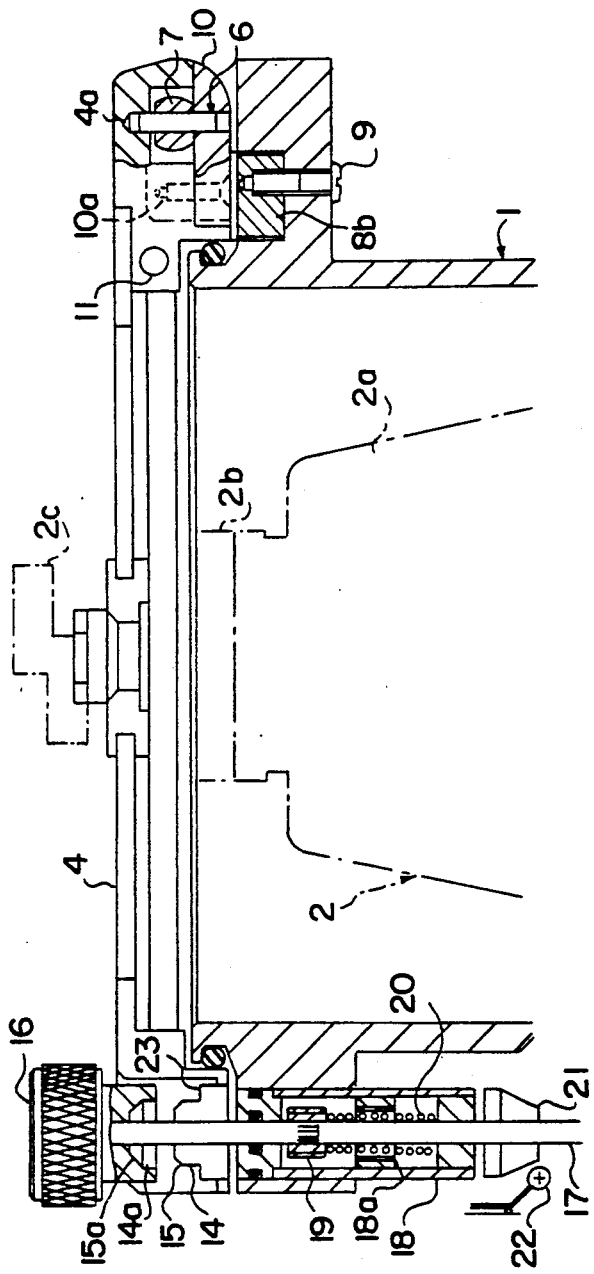

DEVICE FOR CLOSING THE CONTAINMENT WELL OF A BLOOD CENTRIFUGATION CELL IN A CENTRIFUGAL MACHINE

BACKGROUND OF THE INVENTION

The invention relates to a device for closing the containment well of a blood centrifugation cell in a centrifugal machine.

Blood centrifugation is well known for separation of its fraction components such as plasma, white cells, red cells, etc. The process is conducted in blood centrifugation cells having a rigid rotatable container and a stationary joint connected to ducts for the inflow of the blood and for the outflow of the respective separated fractions. In order to perform the centrifugation, the cell is inserted in a well and the container is locked onto a rotatable chuck at the base of a centrifugal machine. The stationary joint is kept in position by a device which closes the inlet of the well and which also confines the space inside the well, isolating it to avoid the escape of blood if the cell should break. The most advanced well closure devices of the prior art are those which leave the ducts connected to the stationary joint outside the well, thus ensuring an easy assembly and optimum sealing; however, it is impossible to integrally clean the well, in particular its inlet.

SUMMARY OF THE INVENTION

An object of the present invention is to provide a device for closing the containment well of a blood centrifugation cell in a centrifugal machine which allows the perfect and integral cleaning of the entire well, particularly the inlet and the immediately adjacent regions.

Another object of the invention is to provide a device which protects the integrity of the stationary joint of the cell and of the ducts connected thereto during the opening and closure operations and furthermore gives the maximum assurances of safety during the procedure.

The proposed objects are achieved by a device for closing the inlet of a containment well of a blood centrifugation cell in the body of a centrifugation machine characterized by a plate supported at one end of the inlet of the containment well and rotatable about the horizontal axis; said plate having a pair of parallel pins extending perpendicularly from the surface thereof; a pair of half-lids which are each pivotably supported at one end thereof by one of said pins, and having matable inner edges; and means for locking said half-lids into a closure position, whereby said half-lids are rotated downwardly against the inlet and with said half-lids pivoted together, thereby closing the inlet of the containment well.

DETAILED DESCRIPTION

Further characteristics and advantages will become apparent from the description of a preferred but not exclusive embodiment of the invention, illustrated only by way of non-limitative example in the accompanying drawings, wherein:

FIG. 2 is a partially sectional side view of the invention;

FIG. 3 is a sectional view taken along the plane III—III of FIG. 1;

FIG. 4 is a perspective view of a mounting plate with its related supports.

Figure 1:
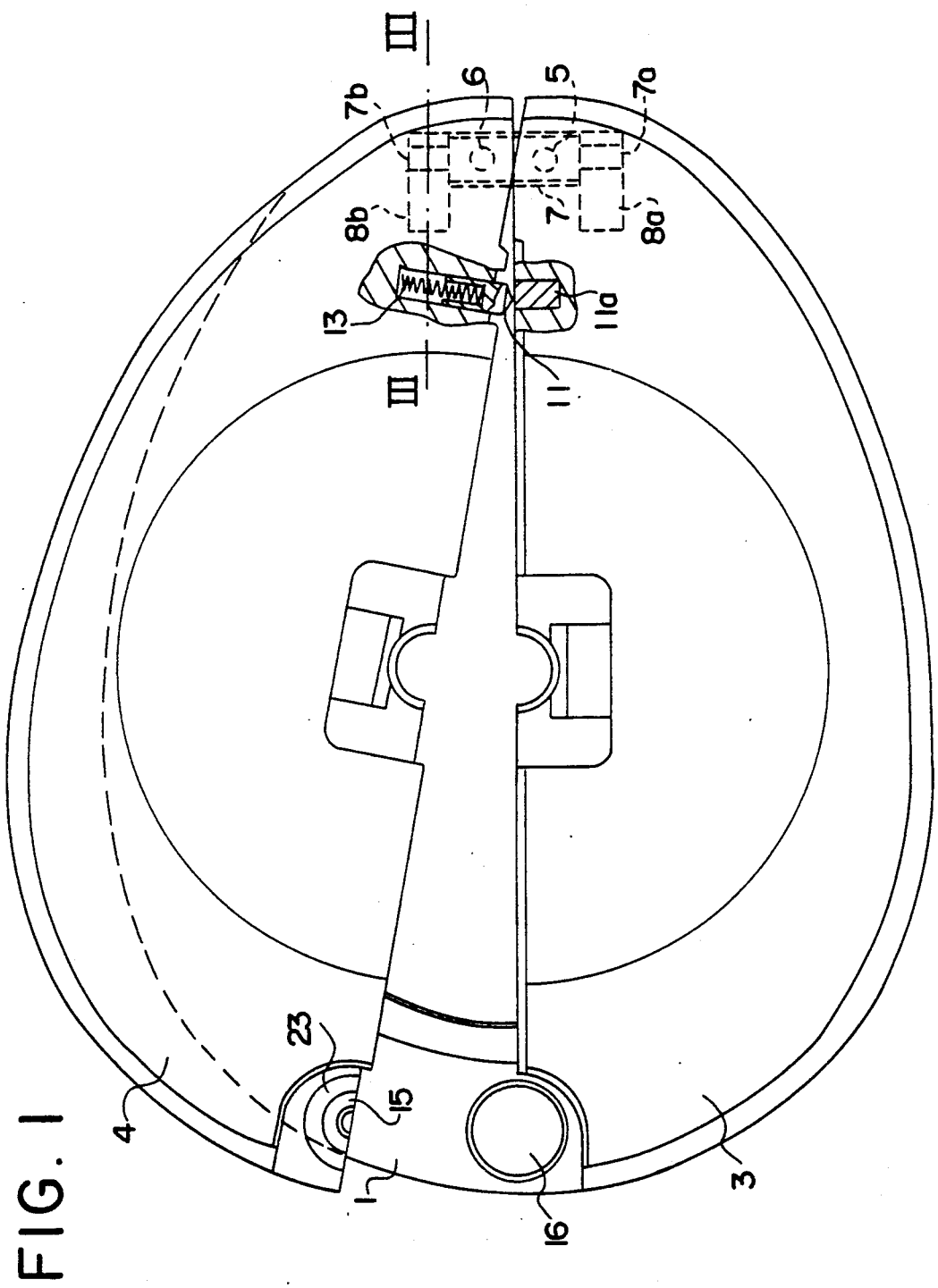
FIG. 1 is a plan view of the invention, with one half-lid in closed position and the other half-lid arranged so as to adhere to the inlet of the well but in open position.

With reference to the above figures, particularly FIG. 2, a containment well 1, is included within a centrifugal machine, for enclosing a blood centrifugation cell 2, (shown in phantom lines) in which a container 2a is rotated by being connected to a rotating chuck (not shown). A stationary joint 2b is provided with couplings 2c for conveyance ducts for the inlet of blood and for the extraction of the separated fractions.

Referring also to FIG. 1, the device for closing the well comprises a pair of half-lids 3 and 4 which have mating inner edges and which can be both spread apart and rotated from one end. The half-lids are pivotable in a divaricated manner at one end, respectively on two parallel axes provided by pins 5 and 6 which extend generally perpendicularly from a plate 7. The plate 7 is provided with two horizontal end pivots 7a and 7b which engage corresponding holes provided in two supports 8a and 8b which are secured by screws 9 to the body at one end of the well 1. The plate 7 facilitates the rotation of the half-lids upwardly for an open configuration and downwardly in a position to close the well.

The method of pivoting of the half-lids 3 and 4 on the respective axes is described in more detail by referring also to FIGS. 3 and 4. It can be seen that the rotational axis of half-lid 4 is provided by the upper pin 6a and which extends from the upper side face of the plate 7 and rotatably engages a hole 4a provided within the half-lid 4, while the lower pin 6b engages a corresponding hole provided in a plate 10. A screw 10a secures the plate 10 to the half-lid 4 to pivotably secure the half-lid to the plate 7. Half-lid 3 is similarly secured to the plate on pin 5.

The half-lids 3 and 4 are provided with elastic means adapted to mutually space them by rotation about the pins 5 and 6. A small round-headed cylinder 11, is slidably accommodated in a hole 12 provided within the half-lid 4 and is pushed by a spring 13 against the facing surface of the half-lid 3, which is provided, in the region of contact, with 25 the metallic abutment 11a.

In operation, the two half-lids 3 and 4 are always intrinsically mutually spread apart in a divaricated manner by the action of the cylinder 11, on abutment 11a. This occurs regardless of the orientation of the plate 7 about its axis of rotation. Only the voluntary action of an operator can move the half-lids mutually closer until they are in contact, overcoming the action of the spring 13 within the cylinder 11. Thus, when it is necessary to access the inside of the well 1 to insert a cell 2, the half-lids 3 and 4 are rotated into the completely raised position and are naturally divaricated, as mentioned. It should be noted that in this position of the half-lids, the well and its adjacent regions are completely available for integral cleaning. Once the cell 2 is inserted, the half-lids are pivoted downwardly by the rotatability of the plate 7 and are lowered in the spread open condition so as to not compromise or interfere with the stationary joint 2b or with the related couplings 2c of the ducts. When the half-lids make contact with the inlet of the well, the operator approaches the half-lids 3 and 4 to move the mating inner edges into mutual contact and locks them in this "closure position". The locking means is shown particularly in FIGS. 2 and 3, and comprise two projections each of which is rigidly associated with each half-lid. The projections are symmetrical halves which form a cylindrical portion 14 and an integral upper conical portion 15 formed when the half-lids are in the closure position. (The projection associated with the half-lid 4 is visible in FIG. 1.) The half-lids 3 and 4 are locked together by the engagement of the projections 14 and 15 within a correspondingly shaped conical recess 15a and cylindrical recess 14a in an actuation knob 16. The actuation knob 16 is fixed at the upper end of a vertically oriented rod 17. The rod is slidably and rotatably supported within a cylindrical sleeve 18 which is rigidly associated with the body of the well 1. The rod includes a threaded portion 19 adapted to engage with female thread 18a which is rigidly associated with the sleeve 18. A spring 20 is interposed between the bottom of the sleeve 18 and the threaded portion 19 of the rod 17. A cam 21 is also rigidly associated with the rod 17 for actuating a sensor 22 which is used in conjunction with circuitry to enable safe operation of the centrifugal machine only when the half-lids are in the closure position.

In order to lock the half-lids 3 and 4 in closure position, the operator, starting from the condition illustrated in FIG. 2, pushes the knob 16 downward, overcoming the action of the spring 20, until the threaded portion 19 makes contact with the female thread 18a; at this point the knob is rotated to engage the threads which further engages the portions 14a and 15a of knob 16 to lock over and around portion 14 and 15 of the projections. After a few turns of the threads, the base of the knob 16 makes contact with a base plane 23. At this point, the cam 21 has moved to actuate the sensor 22 which enables the start-up of the centrifugage, since the half-lids have been completely closed into the closure position.

At the end of the centrifugation, the operator unscrews the knob 16. The cam 21 immediately moves the sensor 22, which operates with the circuitry to provide a suitable indicator to prevent the release of the half-lids while the cell has not completely stopped rotation. Premature opening of the half-lids is further avoided because even during the unscrewing operation, the cylindrical portion 14a of the recess remains in contact with the cylindrical portion 14 of the projection, and therefore the half-lids cannot abandon their mutual contact. In the time used by the operator to disengage the threads, the cell stops its motion, after which the knob 16 can be raised, allowing the half-lids to spread apart in the divaricated manner, and the half-lids can be rotated upwardly to open the well.

The described invention is susceptible to numerous modifications and variations, all of which are within the scope of the inventive concept: all the details may furthermore be replaced with other technically equivalent elements.

In the practical embodiment of the invention, the materials employed, as well as the shapes and dimensions, may be any according to the requirements.

What is claimed is:

1. A device for closing the inlet of a containment well of a blood centrifugation cell in the body of a centrifugation machine characterized in that it comprises:
   a containment well for the blood centrifugation cell;
   a plate supported at one end of the inlet of the containment well and rotatable about the horizontal axis;
   said plate having a pair of parallel pins extending perpendicularly from the surface thereof, each pin having a rotational axis;
   a pair of half-lids which are each pivotally supported at one end and thereof by one of said pins for rotation about the respective axes of the pins in a plane perpendicular to the pins, and the half lids having matable inner edges;
   means for biasing the half-lids normally into a mutually spread-apart, pivoted open configuration; and
   means for locking said half-lids into a closure position, the means for locking including projections on the half lids rigidly associated with each half-lid as symmetrical halves for forming a cylindrical portion and an upper conical portion held by an actuation knob carried on the containment well for movement, the actutation knob having a corresponding recess so that when the half-lids are rotated downwardly against the inlet and with said half-lids pivoted together, thereby closing the inlet of the containment well.

2. A device according to claim 1 wherein said locking means further comprises a sensor means for enabling the operation of the machine only when the closure position of the half-lids is positively achieved.

3. A device according to claim 1, characterized in that said locking means comprises the symmetrical halves which extend from each of said half-lids at the end opposite said pins; and an actuation knob having a recess for engaging the symmetrical halves when said half-lids are rotated downwardly and together into the closure position.

4. A device according to claim 3 wherein said locking means further comprises:
   a sleeve fixed vertically within the body of the machine and aligned with said projections, and having female threads along a portion thereof;
   a rod slidably and rotatably supported within said sleeve, and having a threaded portion for engaging the threads within said sleeve;
   said knob fixed at the upper end of said rod;
   a spring interposed between said rod and said sleeve to bias said knob into a normally unlocked upward position;
   whereby when said half-lids are arranged into the closure position, the knob can be pushed downwardly so that the recess can engage the projections and the knob can be rotated to engage the respective threads to lock the half-lids into the closure position.

5. A device according to claim 4 wherein said rod further includes a cam for contacting a sensor for indicating when said half-lids are in the closure position.

* * * * *